United States Patent

Bridges

[11] Patent Number: 6,027,512
[45] Date of Patent: Feb. 22, 2000

[54] HAIR FOLLICLE HARVESTING DEVICE

[76] Inventor: Ronzee M. Bridges, 26 Dover Cir., Bossier City, La. 71111

[21] Appl. No.: 09/316,570

[22] Filed: May 21, 1999

Related U.S. Application Data

[60] Provisional application No. 60/087,372, May 28, 1998.

[51] Int. Cl.[7] .................................................. A61B 17/50
[52] U.S. Cl. ............................................................. 606/131
[58] Field of Search ............................. 606/36, 133, 131, 606/211, 43, 44, 187

[56] References Cited

U.S. PATENT DOCUMENTS

| | | |
|---|---|---|
| 3,831,202 | 8/1974 | Hulsen . |
| 3,998,230 | 12/1976 | Miller . |
| 5,527,330 | 6/1996 | Tovey . |
| 5,578,054 | 11/1996 | Arnold . |
| 5,611,811 | 3/1997 | Goldberg . |
| 5,693,064 | 12/1997 | Arnold . |
| 5,782,843 | 7/1998 | Aasberg .................................. 606/133 |
| 5,782,851 | 7/1998 | Rassman .................................. 606/133 |
| 5,827,217 | 10/1998 | Silver et al. ............................. 606/131 |

*Primary Examiner*—Jeffrey A. Smith
*Assistant Examiner*—Eduardo C. Robert
*Attorney, Agent, or Firm*—John M Harrison

[57] ABSTRACT

A hair follicle harvesting device which is characterized by a pencil-like harvesting tube fitted at the distal end with a needle of selected bore size for insertion over one or more hairs and hair follicles in a scalp flap and puncturing the scalp flap. The harvesting tube is connected at the proximal end to a source of saline solution and accommodates a flow of saline solution through a venturi or tube constriction by operation of a pump to remove the encircled and loosened hair follicles as micrografts, minigrafts and hair plugs from the scalp flap. The hair follicles are caused to flow through the needle and into the saline solution stream by reduced pressure responsive to flow of the saline solution through the venturi or tube constriction located near the base of the needle in the harvesting tube. The saline stream containing the hair follicles is then directed from the harvesting tube through a screen in a disposable follicle harvesting apparatus or a screen in a follicle collection vessel, which retains the hair follicles on the screen and returns the saline solution to the pump for continued circulation through the harvesting tube. The screen is periodically removed from the harvesting apparatus or follicle collection vessel to collect the harvested hair follicles, which are then used in conventional hair transplant procedures.

31 Claims, 2 Drawing Sheets

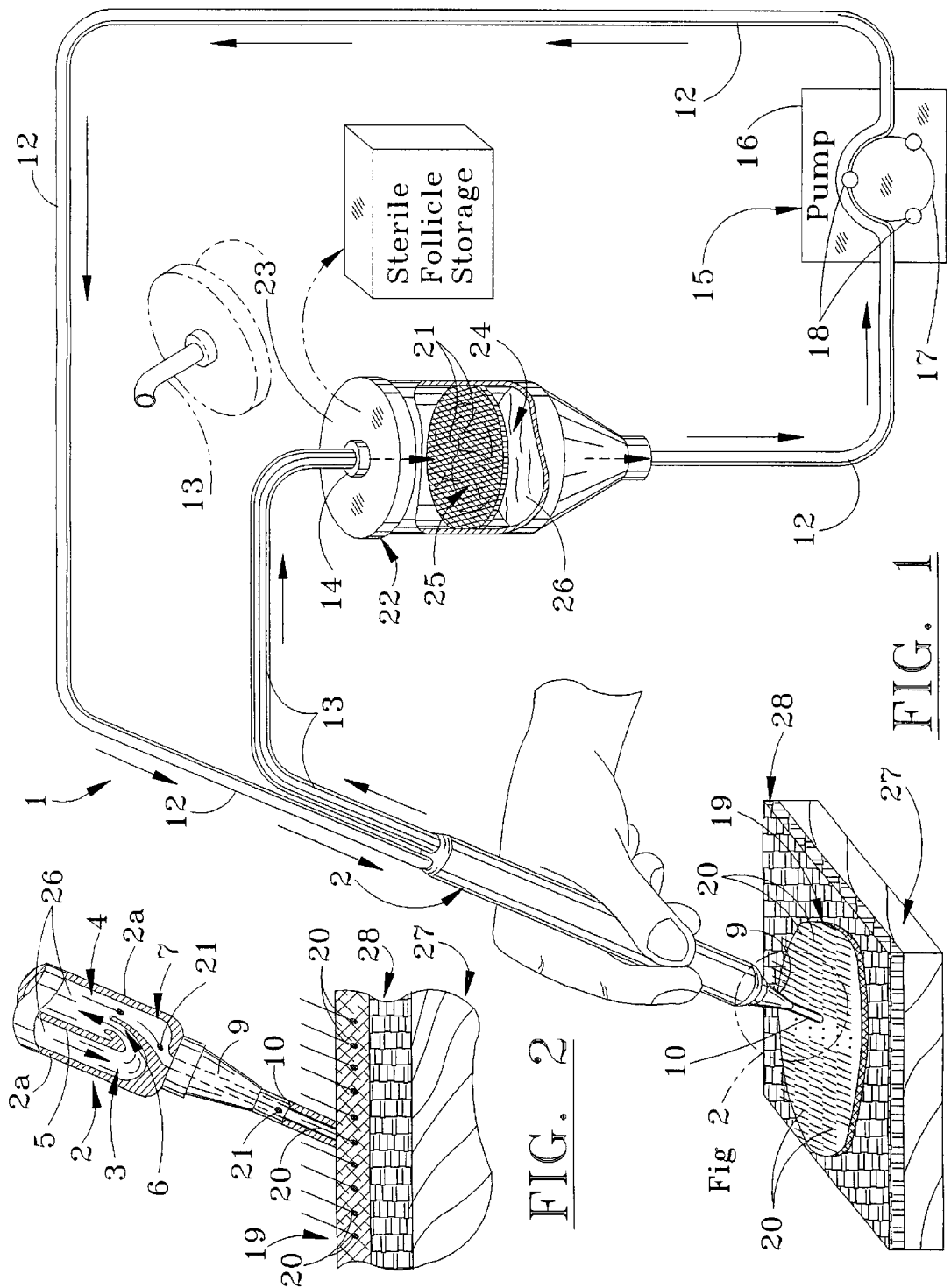

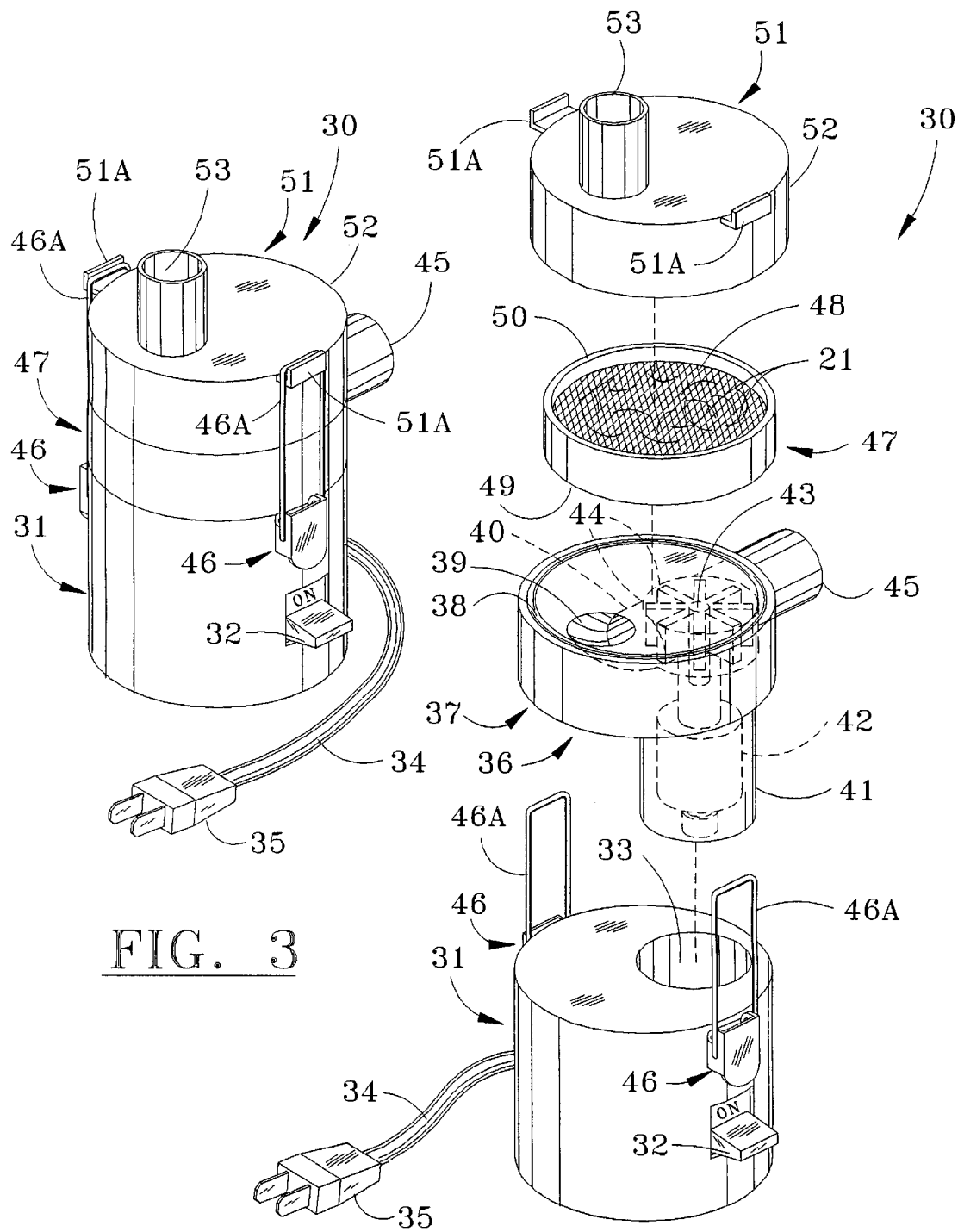

HAIR FOLLICLE HARVESTING DEVICE

CROSS-REFERENCE TO RELATED APPLICATIONS

This application claims the benefit of copending U.S. Provisional Application Serial No. 60/087,372, filed May 28, 1998.

FIELD OF THE INVENTION

This invention relates to hair transplantation techniques and more particularly, to a hair follicle harvesting device which is designed to harvest hair follicles in micrograft, minigraft and hair plug sizes for use in hair transplantation procedures. In a preferred embodiment the hair follicle harvesting device of this invention is characterized by a hollow, elongated, hand-held harvesting tube having a pair of internal passageways, tubes or lumens to facilitate a flow of sterile saline solution through the passageways and through a venturi tube or constriction (hereinafter called venturi) connecting the passageways. The venturi is shaped in the bottom or distal end of the harvesting tube at the base of a needle which is threaded or otherwise fitted to the distal end of the harvesting tube. The needle is typically positioned to encircle one or more hairs and hair follicles in a fixedly-mounted scalp flap harvested from a hair transplant candidate and is then inserted into the scalp surrounding the hair follicles to puncture the scalp and define and loosen a micrograft, minigraft or hair plug, depending upon the gauge or bore size of the needle. The flow of saline solution through the respective passageways, tubes or lumens and the venturi in the harvesting tool creates a vacuum or zone of low pressure at the venturi and the base of the needle in the harvesting tube to facilitate removal of the loosened hairs and hair follicles into the outgoing saline stream. The saline stream is then pumped by means of an external pump from the harvesting tube through a follicle collection vessel or routed to a disposable follicle harvesting apparatus which has a self-contained pump, both vessels having a removable top or lid and fitted with an internal perforated plate or screen, such that the hair follicles are deposited and collected on the plate or screen, while the saline solution continues flowing back through the harvesting tube. The hair follicle harvesting device of this invention facilitates a continuing removal of hair follicles as micrografts, minigrafts and hair plugs in the harvesting tube and depositing of the hair follicles on the perforated plate or screen in the follicle collection vessel or the disposable follicle collection apparatus. The follicle collection process continues until a sufficient number of hair follicles are deposited on the perforated plate or screen to require removal of the plate or screen and the collected hair follicles through the removable collection vessel lid or by disassembling the harvesting apparatus. The choice of harvesting micrografts, minigrafts or hair plugs from the scalp flap is determined by the bore or gauge of the harvesting needle attached to the harvesting tube.

There have been many hair transplant, replant and harvesting techniques proposed and used in the art to replace thinning hair in receding hair lines. For many individuals, hair loss is undesirable and the choice of various techniques for alleviating the hair loss depends upon the extent of the hair loss. These procedures include hair weaving, hairpieces and the use of chemical agents such as "Rogaine" (trademark) and other so-called hair growth enhancers, as well as skin grafts. One of the primary difficulties in the course of undertaking hair transplantation is the difficulty of harvesting hair follicles and repositioning skin grafts from the areas of the head having thicker hair for transplantation to the areas of thinning hair. It is usually advantageous to harvest the hair follicles individually so that a more natural hairline can he achieved and to avoid the necessity of taking large patches of skin and grafting these grafts onto the bald areas. Conventional hair follicle harvesting techniques typically include labor-intensive harvesting procedures involving two to four technicians using razor blades or scalpels to harvest approximately 1000 hair follicles or groups of follicles as micrografts, minigrafts and hair plugs in a three to four hour period of time.

DESCRIPTION OF THE PRIOR ART

U.S. Pat. No. 3,831,202, dated Aug. 27, 1974, to Wayne D. Hulsen, details a "Hair Implant and Process". The process includes using a base member such as a thin, flexible, formed plastic sheet provided with multiple needles, to each of which needles is attached a tuft of hair. In a surgical procedure a section of the patient's scalp is lifted, the base is inserted on the scalp with the needles piercing the scalp section and the section of lifted scalp is replaced to cover the base. Each needle is then withdrawn from the base and scalp, pulling a companion tuft of hair through the needle hole, leaving an area of hair secured within the scalp. U.S. Pat. No. 3,998,230, dated Dec. 21, 1976, to Paul W. Miller, details a "Hair Transplant Process" which includes the steps of inserting an end of a hollow outer needle into the skin to form a pit in the surface of the skin, sliding an inner needle within the outer needle to position an end of the inner needle for supporting an end of a hair within the skin pit adjacent to the end of the outer needle and extracting the outer and inner needles from the skin pit. U.S. Pat. No. 5,527,330, dated Jun. 18, 1996, to H. Jonathan Tovey, details a "Fluid Cutting Instrument" which is adapted for coupling to an external high pressure fluid source and an external vacuum source. The external pressure fluid source and vacuum source operate an irrigation tube configured for coupling to the high pressure fluid source, and the distal end of the irrigation tube forms a nozzle to direct a fluid at high pressure against the tissue to be cut. A suction tube is provided for coupling to the external vacuum source to receive and suction away waste fluid and separated tissue. U.S. Pat. No. 5,578,054, dated Nov. 26, 1996, to James E. Arnold, details a "Method For Hair Transplantation". According to the method of this patent an instrument having a shaft and a blade attached to the shaft normal to the axis of the shaft, is inserted into the skin to a preselected depth determined by a stop disposed along the shaft, to form an incision. The instrument is removed from the skin and a graft of skin having at least one hair is placed in the incision. U.S. Pat. No. 5,611,811, dated Mar. 18, 1997, to Paul M. Goldberg, details a "Micro and Mini Hair Transplant Device". The device includes a device for puncturing the scalp, an element for containing the hair grafts to be transplanted, an element for ejecting the hair grafts from the containing device and a part for actuating the ejecting device, as well as a part for delivering the hair grafts to the transplant site. U.S. Pat. No. 5,693,064, dated Dec. 2, 1997, to James E. Arnold, details a "Dermal Punch For Hair Transplantation and Methods". According to the method an instrument is provided having a concentric, cylindrical shaft with a proximal end, a distal end and an axis extending between the proximal and distal ends. A blade is provided on the distal end of the shaft normal to the axis of the shaft and an escape port is provided in the wall of the shaft near the distal end. The instrument is inserted into the skin to a preselected depth, where the skin is below the escape port, to form a cylindrical incision. The instrument is then removed from the skin. The step of inserting the instrument into the skin is then repeated, with any accumulated skin in the shaft being forced through the escape port. A graft of skin having at least one hair is then placed into at least one of the cylindrical incisions.

It is an object of this invention to provide a new and improved hair follicle harvesting device for continually harvesting hair follicles from a scalp flap for use in hair transplantation procedures.

Another object of the invention is to provide a hair follicle harvesting device which is characterized by a hand-held, fluid-operated hair follicle removing device coupled to a continuous flow hair follicle deposition and collection or harvesting vessel or apparatus, whereby hair follicles are continually and selectively removed by vacuum from a segment of scalp by the hair follicle removal device as micrografts, minigrafts and hair plugs, and deposited on a perforated plate or screen in the hair follicle collection or harvesting vessel or apparatus to accumulate hair follicles for hair transplantation procedures.

Still another object of this invention is to provide a hair follicle harvesting device which is characterized by a hand-operated, hollow pen or pencil-like harvesting tube having a fluid inlet compartment or tube and a fluid outlet compartment or tube connected at a venturi tube or constriction, which constriction, venturi tube or venturi is located near the distal end of the harvesting tube where a needle of selected gauge is attached, typically by threads or a luer-lock device, to the harvesting tube. The saline solution is caused to flow through the inlet compartment, the venturi tube or venturi and the outlet compartment of the harvesting tube to a hair follicle collection device or a disposable hair follicle harvesting vessel by means of a separate or self-contained pump. Accordingly, insertion of the needle over one or more hairs and hair follicles into a scalp flap effects dislodgement of the hairs and hair follicles from the scalp flap as micrografts, minigrafts or hair plugs by reduced pressure. The hair follicles are then pulled into the needle and the outgoing saline solution stream by the reduced saline fluid pressure at the venturi, for accumulation on the perforated plate or screen in the hair follicle collection device or disposable harvesting vessel.

Yet another object of this invention is to provide a hair follicle harvesting device which includes an elongated, hand-operated hair follicle harvesting tube provided in fluid connection with a hair follicle harvesting or collection vessel. The hair follicle harvesting tube includes a hollow, typically cylindrical vessel fitted with a needle at the distal end, the bore of which needle is sufficiently large to encompass one or more hairs and hair follicles in a typically fixedly-mounted scalp flap. The harvesting tube is divided into a fluid inlet compartment, lumen or passageway and a fluid outlet compartment, lumen or passageway, connected to corresponding saline solution inlet and outlet lines, respectively, at the proximal end of the harvesting tube. The inlet and outlet compartments, lumens or passageways are joined at a venturi or constriction at the base of the needle and the venturi or constriction defines a low pressure follicle collection plenum or zone in the fluid outlet compartment, lumen or passageway of the harvesting tube. In a first embodiment the follicle collection vessel is typically characterized by a container which houses a perforated follicle collecting plate or screen for receiving and collecting hair follicles loosened by the needle on the harvesting tube. These hair follicles are pulled into the constricted low pressure follicle collection plenum or zone and into the saline solution stream flowing through the fluid outlet compartment, lumen or passageway by operation of a pump, to the follicle collection vessel. The hair follicles are collected on the perforated plate or screen located in the follicle collection vessel as micrografts, minigrafts and/or hair plugs, depending upon the gauge of the needle, and are periodically harvested from the screen by removal of the vessel lid. In another embodiment of the invention the collecting plate or screen is removably sandwiched between a disposable intake lid and pump assembly, the latter of which includes a pump rotor and blades for pumping saline solution when the pump rotor is inserted in a motor base housing a motor stator. The rotor/stator motor elements effect rotation of the blades and pumping of the saline solution through the harvesting tube and the collecting plate or screen.

A still further object of this invention is to provide a method of harvesting hair follicles from a scalp or scalp flap, which method includes the steps of providing a hair follicle harvesting tube having a fluid inlet and a fluid outlet with a needle for isolating and loosening one or more hair follicles in the scalp or scalp flap; providing a venturi or constriction in the fluid outlet for creating a zone of low pressure in the fluid outlet and the needle and causing the isolated hair follicles to flow through the needle into the fluid outlet; and providing a follicle collection vessel or disposable harvesting apparatus in fluid communication with the fluid outlet and a screen in the follicle collection vessel or harvesting apparatus for collecting the hair follicles on the screen in the follicle collection vessel or disposable harvesting apparatus.

SUMMARY OF THE INVENTION

These and other objects of the invention are provided in a new and improved hair follicle harvesting device and method of harvesting hair follicles, which device is characterized in a preferred embodiment by a hollow, elongated harvesting tube designed for hand operation and fitted with a saline fluid inlet tube, passageway or compartment connected to a saline fluid outlet tube, passageway or compartment at a venturi or constriction, which venturi is located at the base of a needle fitted to the distal end of the harvesting tube. The selectively-sized needle is adapted to fit over one or more hair follicles in a fixed scalp segment or flap and penetrate the scalp for loosening the hair follicles as micrografts, minigrafts or hair plugs, depending upon the needle gauge or bore, thus facilitating loosening and entry of the hair follicles into the fluid stream flowing through the fluid outlet compartment to a zone of low pressure created by operation of the venturi or constriction. The saline stream flows from an outlet tube or passageway to a follicle collection vessel or a disposable harvesting vessel or container, each of which includes a perforated plate or screen for receiving and collecting the hair follicles from the saline stream, which stream is then, in one embodiment, directed from the follicle collection vessel to a pump and is recycled by the pump to the harvesting tube through the inlet tube or passageway. In another embodiment the plate or screen is disposable and is removably seated between a disposable intake lid and pump assembly, which pump assembly engages a typically nondisposable motor base for pumping the saline solution through the system. The dislodged hair follicles are periodically deposited on the screen in the follicle collection vessel or disposable plate or screen and are maintained in a moist, viable condition by the incoming saline solution. In the collection vessel, the collected hair follicles are periodically removed from the screen as micrografts, minigrafts and/or hair plugs by removing or hingedly opening a lid which closes the follicle collection vessel. In the disposable harvest apparatus embodiment the disposable intake lid is removed for access to the removable screen, which can then be removed and discarded after collection of the hair follicles.

The invention includes a method of harvesting hair follicles as micrografts, minigrafts and hair plugs by using a hair follicle harvesting tube fitted with a needle of selected gauge to isolate and loosen the hair follicles in a segment or flap of scalp; circulating saline solution through a venturi in the harvesting tube to flow the hair follicles from the scalp flap or segment into an outgoing saline stream by vacuum; and circulating the saline solution through a follicle collection vessel or a self-contained pumping and harvesting apparatus fitted with a removable and disposable screen for collecting the hair follicles on the screen and recycling the saline solution to the harvesting tube by means of a pump.

BRIEF DESCRIPTION OF THE DRAWINGS

The invention will be better understood by reference to the accompanying drawings, wherein:

FIG. 1 is a perspective view, partially in schematic, illustrating a preferred embodiment of the hair follicle harvesting device of this invention, including the harvesting tube, a follicle collection vessel and a pump for circulating saline solution through the follicle collection vessel and the harvesting tube;

FIG. 2 is a side sectional view of the bottom end of the harvesting tube and a typical scalp flap mounted on a foam rubber pad seated on a scalp flap platform; and FIG. 3 is a perspective, view of an alternative self-contained screening and pumping harvesting apparatus for use with the harvesting tube.

FIG. 4 is a perspective exploded view of the alternative self-contained screening and pumping harvesting apparatus of FIG. 3.

DESCRIPTION OF THE PREFERRED EMBODIMENTS

Referring initially to FIGS. 1 and 2 of the drawings, the hair follicle harvesting device of this invention is generally illustrated by reference numeral 1 and includes a hand-held, hollow, generally pencil or pen-shaped harvesting tube 2, having a tube wall 2a that encloses or defines a fluid inlet passageway or compartment 3 and an adjacent fluid outlet passageway or compartment 4, further defined by a compartment divider 5 (FIG. 2). A venturi 6 is located in the distal end of the harvesting tube 2 and connects the fluid inlet passageway or compartment 3 to the fluid outlet passageway or compartment 4, at the point where a needle 10 is threaded or otherwise seated on a needle mount 9 on the harvesting tube 2. A follicle collection zone or plenum 7 of low fluid pressure is defined in the distal end of the harvesting tube 2 immediately adjacent to and below the venturi 6 and adjacent to the hollow needle mount 9, for purposes which will be hereinafter described. A fluid inlet tube 12 is connected to the fluid inlet passageway or compartment 3 in the harvesting tube 2 and a fluid outlet tube 13 is attached to the fluid outlet passageway or compartment 4 in the harvesting tube 2, as further illustrated in FIG. 1. Accordingly, it will be appreciated from a consideration of FIGS. 1 and 2 that in a first embodiment, fluid such as a sterile saline solution 26 (FIG. 2) may be circulated through the fluid inlet tube 12, the fluid inlet passageway or compartment 3 and the constricted venturi 6 and from the harvesting tube 2 through the fluid outlet passageway or compartment 4 and the fluid outlet tube 13, by operation of a pump 15 (FIG. 1). The pump 15 is typically characterized by a pump housing 16 having a pump rotor 17, fitted with spaced-apart rotor nodes or nodules 18 that sequentially roll against the fluid inlet tube 12 and pump fluid through the fluid inlet tube 12, as further illustrated in FIG. 1.

Referring again to FIGS. 1 and 2 of the drawings, when the saline solution 26 is pumped through the fluid inlet tube 12 by operation of the pump 15, it is circulated through the fluid inlet passageway or compartment 3 and the venturi 6, where it speeds up and then flows through the fluid outlet passageway or compartment 4. The increase in the flow rate of the saline solution 26 in the constricted venturi 6 causes a vacuum or zone of low pressure to develop in the follicle collection plenum 7, illustrated in FIG. 2. Since the follicle collection plenum 7 lies adjacent to the base of the needle 10 at the hollow interior of the needle mount 9, selected growing hair follicles 20 in the scalp flap 19 are subjected to a corresponding vacuum or low pressure zone which extends from the follicle collection plenum 7 and operates through the hollow interior of the needle 10 as the distal end of the needle 10 is inserted over the growing hair follicles 20 and penetrates the fixed scalp flap 19 (FIG. 2). The scalp flap 19 is typically harvested from a donor and mounted on a foam rubber pad 28 which is, in turn, typically secured to an underlying, usually wood, scalp flap platform 27, as further illustrated in FIG. 2. Accordingly, when the distal end of the needle 10 is inserted into the scalp flap 19, thus encircling and isolating one or more of the growing hair follicles 20 in microgram, minigraft or hair plug size, depending upon the selected bore size or gauge of the needle 10, the isolated growing hair follicles 20 are loosened in the scalp flap 19. The loosened growing hair follicles 20 are thusly removed from the scalp flap 19 through the hollow interior of the needle 10 by operation of the vacuum or low pressure exerted through the follicle collection plenum 7 inside the needle 10 and the hollow interior of the needle mount 9, by the saline solution 26 flowing through the venturi 6. Accordingly, in the first embodiment of this invention the detached harvested hair follicles 21 are vacuum-transported upwardly from the scalp flap 19 as a micrograft, minigraft or hair plug, through the hollow interior of the needle 10, the hollow needle mount 9 and into the follicle collection plenum 7 and the fluid outlet passageway or compartment 4, where they are then carried by the outwardly-flowing saline solution 26 through the fluid outlet tube 13 to the follicle storage vessel 22, illustrated in FIG. 1. The saline solution 26 is then introduced into the interior of the follicle storage vessel 22 through an opening in the vessel lid 23 at the rubber seal 14, as illustrated in FIG. 1 and the entrained harvested hair follicles 21 are retained on a perforated plate or screen 25, while the saline solution 26 flows through the screen openings and pools in the bottom of the typically funnel-shaped follicle storage vessel 22. The hair follicle-free saline solution 26 is pumped from the bottom of the follicle storage vessel 22 back into the fluid inlet tube 12 by operation of the pump 15, as heretofore described, and continually moistens the harvested hair follicles 21 collected on the screen 25 as it flows into the follicle storage vessel 22. It will be appreciated by those skilled in the art that the harvested hair follicles 21 can be quickly and easily removed from the interior of the follicle collection vessel 22 by simply terminating the flow of saline solution through the hair follicle harvesting device 1 by stopping the pump 15 or by alternative methods, and removing or hingedly lifting the vessel top or lid 23, as well as the screen 25 upon which the harvested hair follicles 21 rest. The harvested hair follicles 21 can then be collected, organized in any desired manner and used in various hair transplantation techniques known to those skilled in the art.

In a second embodiment and referring to FIG. 3 of the drawings, the detached harvested hair follicles 21 are vacuum-transported upwardly from the scalp 19 as a micrograft, minigraft or hair plug, through the hollow interior of the needle 10, the hollow needle mount 9 and into the follicle collection plenum 7 and the fluid outlet passageway or compartment 4 as described above, where they are then carried by the outwardly-flowing saline solution 26 through the fluid outlet tube 13 to the intake lid nipple 53 in the intake lid 51 of the disposable hair follicle harvesting device 30, as illustrated in FIG. 3. The intake lid 51 has an intake lid rim 52 which has a pair of lid flanges 51a and fits over a screen frame 47, provided with a recessed screen 48 and having a frame lip 49 and a frame rim 50, as illustrated. Accordingly, the hair follicles 21 are deposited on the screen 48 as the saline solution continues to flow through the screen frame 47 and screen 48 into the underlying saline intake 39 of a pump assembly 36, upon which the screen frame 47 is removably seated at the frame lip 49. The pump assembly 36 is further characterized by an assembly housing 37, provided with a gasket 38 for sealing the intake lid 51 on the assembly housing 37 by means of a latch 46, having wire fingers 46a, for removably engaging the lid flanges 51a when the disposable hair follicle harvesting device 30 is assembled as illustrated in FIG. 3. Saline flowing from the screen 48 enters the saline intake 39 and flows through the internal flow passage 40 provided in the assembly housing 37 and exits the assembly housing 37 through a saline discharge nipple 45. The saline discharge nipple 45 in turn communicates with the fluid inlet tube 12 and thus, the harvesting tube 2 in the same manner as illustrated in FIG. 1. The saline is caused to flow through the flow passage 40 in the assembly housing 37 by means of a magnetic pump rotor 42 which includes a magnetic rotor shaft 43, to which is attached pump blades 44, as further illustrated in FIG. 3. In a preferred embodiment, the pump rotor 42 is placed in a rotor sleeve 41, which is inserted in a rotor access opening 33 provided in an underlying electromagnet field generator or motor base 31 having a switch 32 and electrical wiring 34, fitted with a plug 35. Accordingly, when the disposable hair follicle harvesting device 30 is assembled as illustrated in FIG. 3, with the assembly housing 37 fitted on the motor base 31 and the pump rotor 42 inserted in the rotor access opening 33, operation of the stator (not illustrated) in the motor base 31 causes the pump rotor 42 to rotate inside the rotor sleeve 41 and effect rotation of the rotor shaft 43 and the pump blades 44 to pump the saline solution through the flow passage 40 and from the saline discharge nipple line 45 and connecting fluid inlet tube 12, to the harvesting tube 2 as illustrated in FIG. 1. Access to the hair follicles 21 harvested on the screen 48 can be easily effected by manipulating the latch 46 to remove the intake lid 51 and the screen frame 47 from the assembly housing 37.

It will be further appreciated by those skilled in the art that the hair follicle harvesting device 1 of this invention is characterized by convenience and flexibility, in that the size or gauge of the needle 10 on the harvesting tube 2 can be chosen to encircle one or more growing hair follicles 20 as illustrated in FIG. 2, and isolate the targeted growing hair follicles 20 into micrografts, minigrafts and hair plugs. These harvested hair follicles 21 are vacuum-delivered into the follicle collection plenum 7 and the saline solution 26 flowing through the fluid outlet passageway or compartment 4 of the harvesting tube 2 by operation of the venturi 6, as heretofore described. For example, typical needle sizes such as 18 and 20 gauge, in non-exclusive particular, may be used in the growing hair follicle 20 harvesting process of this invention. For the purposes of this application, a micrograft typically includes one to two follicles, a minigraft encompasses two to four hair follicles and a hair plug includes more than four hair follicles. The degree of suction or vacuum required at the venturi 6 constriction is a function of the flow rate of the saline solution 26 through the venturi 6, as well as the configuration of the venturi 6 and the follicle collection plenum 7. Moreover, referring again to FIG. 1, the circulating flow rate of the saline solution 26 is also a function of the type and size of the pump 15 which is utilized to effect the desired circulation of saline solution 26 through the harvesting tube 2 and the follicle collection vessel 22. In this regard, while the pump 15 is illustrated in the drawing as a rotary pump, it will be appreciated by those skilled in the art that the pump 15 may be a pump of any desired design, including centrifugal, positive displacement or the like, in non-exclusive particular, depending upon the degree of vacuum or low pressure required in the venturi 6 and the follicle collection plenum 7 to vacuum-deliver the targeted micrograft, minigraft or hair plug harvested hair follicles 21 to the follicle collection plenum 7 and into the outflowing stream of saline solution 26. Moreover, as illustrated in FIG. 3, the pump assembly 36 can be utilized with the harvesting tube 2 in place of the pump 15 and follicle collection vessel 22, to implement rotation of the self-contained pump rotor 42 and pump blades 44 and pumping of the saline solution 26 through the removable and disposable screen frame 47 and screen 48, as heretofore described.

It is also understood that while the fluid inlet passageway or compartment 3 and the fluid outlet passageway or compartment 4 of the harvesting tube 2 can be defined by the tube wall 2a and the compartment divider 5, as described above and as illustrated in the drawing, the fluid inlet tube 12 and fluid outlet tube 13 may alternatively be extended into the harvesting tube 2 and connected at a constriction or venturi 6 near the needle mount 9, to achieve the desired zone of low pressure or vacuum in the follicle collection plenum 7.

While the preferred embodiments of the invention have been described above, it will be recognized and understood that various modifications may be made in the invention and the appended claims are intended to cover all such modifications which may fall within the spirit and scope of the invention.

Having described my invention with the particularity set forth above, what is claimed is:

1. A hair follicle harvesting device for harvesting hair follicles from a scalp flap, comprising a harvesting tube having a fluid inlet and a fluid outlet communicating with said fluid inlet to define a juncture for receiving a flow of fluid; a needle provided on said harvesting tube for isolating the hair follicles and loosening the hair follicles in the scalp flap; a venturi provided in said juncture for establishing a vacuum in said fluid outlet of said harvesting tube and said needle responsive to the flow of fluid through said venturi; and a follicle collection vessel provided in fluid connection with said fluid outlet in said harvesting tube, whereby the hair follicles from the scalp flap are caused to flow through said needle and into said fluid outlet and said follicle collection vessel with the flow of fluid, responsive to the vacuum created in said venturi means.

2. The hair follicle harvesting device of claim 1 wherein said venturi comprises a constriction at said juncture for increasing the flow of fluid and reducing the pressure of the flow of fluid at said constriction.

3. The hair follicle harvesting device of claim 1 comprising a follicle collection plenum provided in said fluid outlet of said harvesting tube at said venturi for defining a zone of low pressure in said fluid outlet by operation of said venturi means.

4. The hair follicle harvesting device of claim 1 wherein said venturi comprises a constriction at said juncture for increasing the flow of fluid and reducing the pressure of the flow of fluid at said constriction and comprising a follicle collection plenum provided in said fluid outlet of said harvesting tube at said constriction for defining a zone of low pressure in said fluid outlet by operation of said constriction.

5. The hair follicle harvesting device of claim 1 comprising a screen provided in said follicle collection vessel for receiving and collecting the hair follicles in the flow of fluid from said fluid outlet in said harvesting tube.

6. The hair follicle harvesting device of claim 5 wherein said venturi comprises a constriction at said juncture for increasing the flow of fluid and reducing the pressure of the flow of fluid at said constriction.

7. The hair follicle harvesting device of claim 5 comprising a follicle collection plenum provided in said fluid outlet of said harvesting tube at said venturi for defining a zone of low pressure in said fluid outlet by operation of said venturi.

8. The hair follicle harvesting device of claim 5 wherein said venturi comprises a constriction at said juncture for increasing the flow of fluid and reducing the pressure of the flow of fluid at said constriction and comprising a follicle collection plenum provided in said fluid outlet of said harvesting tube at said constriction for defining a zone of low pressure in said fluid outlet by operation of said constriction.

9. The hair follicle harvesting device of claim 1 comprising a pump connected to said fluid inlet and said follicle collection vessel for pumping the fluid through said harvesting tube and said follicle collection vessel.

10. The hair follicle harvesting device of claim 9 wherein said venturi comprises a constriction at said juncture for increasing the flow of fluid and reducing the pressure of the flow of fluid at said constriction.

11. The hair follicle harvesting device of claim 9 comprising a follicle collection plenum provided in said fluid outlet of said harvesting tube at said venturi for defining a zone of low pressure in said fluid outlet by operation of said venturi.

12. The hair follicle harvesting device of claim 9 wherein said venturi comprises a constriction for increasing the flow of fluid and reducing the pressure of the flow of fluid at said constriction and comprising a follicle collection plenum provided in said fluid outlet of said harvesting tube at said constriction for defining a zone of low pressure by operation of said constriction.

13. The hair follicle harvesting device of claim 9 comprising a screen provided in said follicle collection vessel for receiving and collecting the hair follicles in the flow of fluid from said fluid outlet in said harvesting tube.

14. The hair follicle harvesting device of claim 13 wherein said venturi comprises a constriction in said fluid inlet and said fluid outlet for increasing the flow of fluid and reducing the pressure of the flow of fluid at said constriction.

15. The hair follicle harvesting device of claim 13 comprising a follicle collection plenum provided in said fluid outlet of said harvesting tube at said venturi for defining a zone of low pressure in said fluid outlet by operation of said venturi.

16. The hair follicle of claim 13 wherein said venturi comprises a constriction for increasing the flow of fluid and reducing the pressure of the flow of fluid at said constriction and comprising a follicle collection plenum provided in said fluid outlet of said harvesting tube at said constriction for defining a zone of low pressure in said fluid outlet by operation of said constriction.

17. The hair follicle harvesting device of claim 1 comprising a pump provided in said follicle collection vessel for pumping fluid through said harvesting tube and said follicle collection vessel.

18. The hair follicle harvesting device of claim 17 wherein said venturi comprises a constriction at said juncture for increasing the flow of fluid and reducing the pressure of the flow of fluid at said constriction.

19. The hair follicle harvesting device of claim 17 comprising a follicle collection plenum provided in said fluid outlet of said harvesting tube at said venturi for defining a zone of low pressure in said fluid outlet by operation of said venturi.

20. The hair follicle harvesting device of claim 17 wherein said venturi comprises a constriction for increasing the flow of fluid and reducing the pressure of the flow of fluid at said constriction and comprising a follicle collection plenum provided in said fluid outlet of said harvesting tube at said constriction for defining a zone of low pressure by operation of said constriction.

21. The hair follicle harvesting device of claim 17 comprising a screen provided in said follicle collection vessel for receiving and collecting the hair follicles in the flow of fluid from said fluid outlet in said harvesting tube.

22. The hair follicle harvesting device of claim 21 wherein said venturi comprises a constriction in said fluid inlet and said fluid outlet for increasing the flow of fluid and reducing the pressure of the flow of fluid at said constriction.

23. The hair follicle harvesting device of claim 21 comprising a follicle collection plenum provided in said fluid outlet of said harvesting tube at said venturi for defining a zone of low pressure in said fluid outlet by operation of said venturi.

24. The hair follicle harvesting device of claim 21 wherein said venturi comprises a constriction for increasing the flow of fluid and reducing the pressure of the flow of fluid at said constriction and comprising a follicle collection plenum provided in said fluid outlet of said harvesting tube at said constriction for defining a zone of low pressure in said fluid outlet by operation of said constriction.

25. A hair follicle harvesting device for harvesting hair follicles from a scalp flap, comprising a harvesting tube having a needle at one end thereof for isolating the hair follicles in the scalp flap; a fluid inlet passageway and a fluid outlet passageway provided in said harvesting tube, said fluid outlet passageway connected to said fluid inlet passageway at a passageway junction adjacent to said needle for receiving a flow of saline solution; a venturi constriction provided in said passageway junction for creating a vacuum in said fluid outlet passageway at said needle responsive to the flow of saline solution from said fluid inlet passageway through said venturi constriction to said fluid outlet passageway, said vacuum operable for pulling hair follicles from the scalp flap through the needle and into the saline solution in said fluid outlet passageway; a follicle collection vessel provided in fluid connection with said fluid inlet passageway and said fluid outlet passageway for receiving the saline solution and the hair follicles from said fluid outlet passageway; and a screen provided in said follicle collection vessel for collecting the hair follicles in the saline solution from the flow of saline solution through said follicle collection vessel.

26. The hair follicle harvesting device of claim 25 comprising a follicle collection plenum provided in said fluid outlet passageway of said harvesting tube at said venturi constriction for defining a zone of low pressure in said fluid outlet passageway by operation of said venturi constriction.

27. The hair follicle harvesting device of claim 26 comprising a pump connected to said fluid inlet passageway and said follicle collection vessel for pumping the saline solution fluid through said harvesting tube and said follicle collection vessel.

28. The hair follicle harvesting device of claim 26 comprising a pump provided in said follicle collection vessel for pumping fluid through said harvesting tube and said follicle collection vessel.

29. A method of harvesting hair follicles from a scalp flap comprising providing a harvesting tube having a fluid inlet and a fluid outlet and a needle for isolating the hair follicles in the scalp flap; providing a venturi in said fluid outlet of said harvesting tube for creating a vacuum in said fluid outlet and said needle and causing the hair follicles to flow from the scalp flap through said needle and into said fluid outlet; providing a collection vessel in fluid communication with said fluid outlet in said harvesting tube for collecting the hair follicles from said scalp flap; and isolating at least one hair follicle from the scalp flap with said needle, so that the at least hair follicle flows from the scalp flap through said needle, into the fluid outlet and into the collection vessel.

30. The method of claim 29 comprising providing a pump connecting said harvesting tube and said collection vessel for pumping fluid from said collection vessel through said harvesting tube and from said harvesting tube back to said collection vessel.

31. The method of claim 29 comprising providing a pump in said collection vessel for pumping fluid from said collection vessel through said harvesting tube and from said harvesting tube back to said collection vessel.

* * * * *